(12) United States Patent
Hwang et al.

(10) Patent No.: US 7,141,720 B2
(45) Date of Patent: Nov. 28, 2006

(54) TRANSCRIPTIONAL FACTOR ENHANCING THE RESISTANCE OF PLANTS TO OSMOTIC STRESS

(75) Inventors: Inhwan Hwang, Pohang-si (KR); Hai Lan Piao, Hunchun (CN)

(73) Assignee: Genomine, Inc., Kyungbuk (KR)

( * ) Notice: Subject to any disclaimer, the term of this patent is extended or adjusted under 35 U.S.C. 154(b) by 462 days.

(21) Appl. No.: 10/433,005

(22) PCT Filed: Mar. 9, 2001

(86) PCT No.: PCT/KR01/00364

§ 371 (c)(1), (2), (4) Date: May 29, 2003

(87) PCT Pub. No.: WO02/44389

PCT Pub. Date: Jun. 6, 2002

(65) Prior Publication Data

US 2004/0072289 A1    Apr. 15, 2004

(30) Foreign Application Priority Data

Dec. 2, 2000   (KR) ............................... 2000-72720

(51) Int. Cl.
*C12N 15/82* (2006.01)
*C12N 15/29* (2006.01)
*C07H 21/00* (2006.01)
*A01H 5/00* (2006.01)

(52) U.S. Cl. .................. 800/289; 435/468; 435/320.1; 536/23.1; 536/23.6

(58) Field of Classification Search .................... None
See application file for complete search history.

(56) References Cited

OTHER PUBLICATIONS

Keskin et al. (Protein Science, 13:1043-1055, 2004).*
Thornton et al. (Nature structural Biology, structural genomics supplement, Nov. 2000).*
Guo et al. (PNAS, 101: 9205-9210, 2004).*
Ming Li Wang, et al, "A Cluster of ABA-Regulated Genes on *Arabidopsis thaliana* BAC T07M07," Genome Research (4), pp. 325-333, Apr. 4, 1999.
Ingela Fridborg, et al, "The *Arabidopsis* Dwarf Mutant *shi* Exhibits Reduced Gibberellin Responses Conferred by Overexpression of a New Putative Zinc Finger Protein," The Plant Cell, vol. 11, pp. 1019-1031, Jun. 1999.
Zhongsen Li, et al, "PEI1. an Embryo-Specific Zinc Finger Protein Gene Required for Heart-Stage Embryo Formation in *Arabidopsis*," The Plant Cell, vol. 10, pp. 383-398, Mar. 1998.
Kazuko Yamaguchi-Shinozaki, et al, "Characterization of the expression of a desiccation-responsive rd29 gene of *Arabidopsis thaliana* and analysis of its promoter in transgenic plants," Mol. Gen Genet, vol. 236, pp. 331-340, Jan. 1993.
Kjell-Ove Holmström, et al, "Production of the *Escherichia coli* betaine-aldehyde dehydrogenase, an enzyme required for the synthesis of the osmoprotectant glycine betaine, in transgenic plants," The Plant Journal, 6(5), pp. 749-758, Nov. 1994.

* cited by examiner

*Primary Examiner*—Ashwin Mehta
*Assistant Examiner*—Vinod Kumar
(74) *Attorney, Agent, or Firm*—Buchanan Ingersoll & Rooney PC

(57) ABSTRACT

The present invention relates to a transcription factor of a plant, AtSIZ, induced by osmotic stress; a gene encoding the transcription factor; and a method for enhancing resistance to stress of a plant by using the gene. The AtSIZ protein isolated from *Arabidopsis thaliana* is a polypeptide, which contains a $C_3H$-type zinc finger motif and acts as a transcription regulation factor activating transcription of genes related to stress response of a plant. Therefore, a plant with the enhanced resistance to osmotic stress can be produced by over expressing the AtSIZ gene in the plant through transforming recombinant plasmid containing AtSIZ gene into a plant and consequently, the productivity of the plant can be increased.

12 Claims, 10 Drawing Sheets

FIG.1

AtSIZ

EtBr

A  AtSIZ

B resistance(%)    0±0    70±5

SEQUENCE LISTING

```
<160> NUMBER OF SEQ ID NOS: 8

<210> SEQ ID NO 1
<211> LENGTH: 2273
<212> TYPE: DNA
<213> ORGANISM: Arabidopsis thaliana
<220> FEATURE:
<221> NAME/KEY: CDS
<222> LOCATION: (166)...(1956)
<223> OTHER INFORMATION: gene encoding C3H Zinc protein AtSIZ
<220> FEATURE:
<221> NAME/KEY: misc_feature
<222> LOCATION: 578
<223> OTHER INFORMATION: n = A,T,C or G

<400> SEQUENCE: 1
aattcggcac gaggtaaaaa ccaagttcct tttaaaagga gcctctcctt tctcatttga      60
tccttcttca aaaccccaa ccacttcttc tccccaaaaa cctccaaagt ttcaatcttt     120
acttctctct ttttctccaa gttatcttct tttctaggaa gagat atg tgc ggt gca   177
                                                  Met Cys Gly Ala
                                                   1 aag agc aac ctt tgc tca tct aaa acc cta aca gaa gtc gaa ttc atg      225
Lys Ser Asn Leu Cys Ser Ser Lys Thr Leu Thr Glu Val Glu Phe Met
 5                  10                  15                  20
```

-continued

| | | |
|---|---|---|
| agg cag aaa tca gaa gac gga gct tcc gcc acg tgt ctc ctc gaa ttc<br>Arg Gln Lys Ser Glu Asp Gly Ala Ser Ala Thr Cys Leu Leu Glu Phe<br>             25                             30                            35 | 273 |
| gcc gcc tgt gat gat ctt tca tcg ttt aag aga gag atc gaa gag aat<br>Ala Ala Cys Asp Asp Leu Ser Ser Phe Lys Arg Glu Ile Glu Glu Asn<br>                    40                           45                            50 | 321 |
| cca tcg gtg gag att gat gag tca ggg ttt tgg tat tgc aga cgg gtc<br>Pro Ser Val Glu Ile Asp Glu Ser Gly Phe Trp Tyr Cys Arg Arg Val<br>          55                           60                           65 | 369 |
| ggg tct aag aag atg ggt ttt gaa gaa aga aca cca ctt atg gtt gct<br>Gly Ser Lys Lys Met Gly Phe Glu Glu Arg Thr Pro Leu Met Val Ala<br>70                       75                           80 | 417 |
| gct atg tat gga agc atg gaa gtg ttg aat tac ata att gcc aca gga<br>Ala Met Tyr Gly Ser Met Glu Val Leu Asn Tyr Ile Ile Ala Thr Gly<br>85                       90                           95                        100 | 465 |
| aga tcc gat gtg aac aga gtt tgc agt gac gag aaa gtc act gct ctt<br>Arg Ser Asp Val Asn Arg Val Cys Ser Asp Glu Lys Val Thr Ala Leu<br>                   105                       110                      115 | 513 |
| cac tgt gca gtt tct ggc tgt tct gtt tct atc gtt gag atc atc aag<br>His Cys Ala Val Ser Gly Cys Ser Val Ser Ile Val Glu Ile Ile Lys<br>                   120                       125                      130 | 561 |
| atc ttg ctt gat gct tnt gct tca cct aat tgt gtt gac gct aat ggg<br>Ile Leu Leu Asp Ala Xaa Ala Ser Pro Asn Cys Val Asp Ala Asn Gly<br>             135                       140                      145 | 609 |
| aac aaa ccg gtt gat ttg ttg gct aaa gat tct cgg ttt gtt cct aac<br>Asn Lys Pro Val Asp Leu Leu Ala Lys Asp Ser Arg Phe Val Pro Asn<br>150                      155                        160 | 657 |
| cat agt ata aag gcg gtt gag gtt tta ctg acc ggg att cat ggt tcg<br>His Ser Ile Lys Ala Val Glu Val Leu Leu Thr Gly Ile His Gly Ser<br>165                      170                        175                      180 | 705 |
| gtt atg gaa gaa gag gag gag gaa ctg aag agt gtt gtg act aag tat<br>Val Met Glu Glu Glu Glu Glu Glu Leu Lys Ser Val Val Thr Lys Tyr<br>                   185                       190                      195 | 753 |
| cca gct gat gca tca ctt cct gat att aac gaa ggt gtt tat gga act<br>Pro Ala Asp Ala Ser Leu Pro Asp Ile Asn Glu Gly Val Tyr Gly Thr<br>                   200                       205                      210 | 801 |
| gat gat ttt agg atg ttt agc ttt aag gtt aag cca tgt tct agg gct<br>Asp Asp Phe Arg Met Phe Ser Phe Lys Val Lys Pro Cys Ser Arg Ala<br>             215                       220                      225 | 849 |
| tat tca cat gat tgg act gaa tgt cct ttt gtt cat cct ggt gag aat<br>Tyr Ser His Asp Trp Thr Glu Cys Pro Phe Val His Pro Gly Glu Asn<br>         230                       235                      240 | 897 |
| gca agg agg aga gat cct agg aag tat cct tac act tgt gtg cct tgt<br>Ala Arg Arg Arg Asp Pro Arg Lys Tyr Pro Tyr Thr Cys Val Pro Cys<br>245                      250                        255                      260 | 945 |
| ccc gag ttt cgt aaa ggg tct tgt cct aaa gga gat tcg tgt gag tac<br>Pro Glu Phe Arg Lys Gly Ser Cys Pro Lys Gly Asp Ser Cys Glu Tyr<br>                   265                       270                      275 | 993 |
| gcg cac ggt gtt ttc gag tct tgg ctt cac ccg gcg cag tat agg aca<br>Ala His Gly Val Phe Glu Ser Trp Leu His Pro Ala Gln Tyr Arg Thr<br>             280                       285                      290 | 1041 |
| cgg ctt tgc aaa gat gag act ggt tgt gct agg aga gtt tgt ttc ttt<br>Arg Leu Cys Lys Asp Glu Thr Gly Cys Ala Arg Arg Val Cys Phe Phe<br>         295                       300                      305 | 1089 |
| gct cat aga cgg gat gag tta aga ccg gtt aat gct tct act ggt tct<br>Ala His Arg Arg Asp Glu Leu Arg Pro Val Asn Ala Ser Thr Gly Ser<br>310                      315                        320 | 1137 |
| gca atg gtt tca cca agg tcg tct aat cag tct cct gag atg tct gtt<br>Ala Met Val Ser Pro Arg Ser Ser Asn Gln Ser Pro Glu Met Ser Val<br>325                      330                        335                      340 | 1185 |

| | |
|---|---:|
| atg tct cct ttg acg ctg gga tca tcg cca atg aac tct cct atg gct<br>Met Ser Pro Leu Thr Leu Gly Ser Ser Pro Met Asn Ser Pro Met Ala<br>345 350 355 | 1233 |
| aat ggt gtt cct ttg tct cca aga aat ggt ggt tta tgg cag aac aga<br>Asn Gly Val Pro Leu Ser Pro Arg Asn Gly Gly Leu Trp Gln Asn Arg<br>360 365 370 | 1281 |
| gtt aat agc ctt aca cca cca ccg ttg cag ctt aat ggt agc aga ttg<br>Val Asn Ser Leu Thr Pro Pro Pro Leu Gln Leu Asn Gly Ser Arg Leu<br>375 380 385 | 1329 |
| aag tcg act ttg agt gct ata tat atg gat atg gag atg gaa ctt agg<br>Lys Ser Thr Leu Ser Ala Ile Tyr Met Asp Met Glu Met Glu Leu Arg<br>390 395 400 | 1377 |
| ttt cgc ggt ttg gat aac cgg aga ctt ggt gat ctc aag cca tcc aac<br>Phe Arg Gly Leu Asp Asn Arg Arg Leu Gly Asp Leu Lys Pro Ser Asn<br>405 410 415 420 | 1425 |
| ctc gaa gag act ttc gga tca tat gac tca gct tct gtg atg caa ctt<br>Leu Glu Glu Thr Phe Gly Ser Tyr Asp Ser Ala Ser Val Met Gln Leu<br>425 430 435 | 1473 |
| caa tca cca agc agg cat tct cag atg aac cac tat ccg tct tca cct<br>Gln Ser Pro Ser Arg His Ser Gln Met Asn His Tyr Pro Ser Ser Pro<br>440 445 450 | 1521 |
| gtg agg cag cct cct cct cat gga ttc gaa tct tca gca gcc atg gca<br>Val Arg Gln Pro Pro Pro His Gly Phe Glu Ser Ser Ala Ala Met Ala<br>455 460 465 | 1569 |
| gct gca gtg atg aat gca aga tcc tca gcg ttt gcg aaa cgc agc ttg<br>Ala Ala Val Met Asn Ala Arg Ser Ser Ala Phe Ala Lys Arg Ser Leu<br>470 475 480 | 1617 |
| agt ttc aaa cca gct cca gta gct tct aat gtc tcc gat tgg gga tca<br>Ser Phe Lys Pro Ala Pro Val Ala Ser Asn Val Ser Asp Trp Gly Ser<br>485 490 495 500 | 1665 |
| cca aat ggg aag ctt gag tgg gga atg caa ata tat gag ctg aac aag<br>Pro Asn Gly Lys Leu Glu Trp Gly Met Gln Ile Tyr Glu Leu Asn Lys<br>505 510 515 | 1713 |
| ttg agg aga agt gcc tcc ttc ggc att cat gga aac aac aac aac agt<br>Leu Arg Arg Ser Ala Ser Phe Gly Ile His Gly Asn Asn Asn Asn Ser<br>520 525 530 | 1761 |
| gtg tca cgc cct gct aga gac tac agt gac gag cca gat gtg tcg tgg<br>Val Ser Arg Pro Ala Arg Asp Tyr Ser Asp Glu Pro Asp Val Ser Trp<br>535 540 545 | 1809 |
| gtg aac tca ctg gtg aaa gag aat gca cca gag aga gtg aat gag agg<br>Val Asn Ser Leu Val Lys Glu Asn Ala Pro Glu Arg Val Asn Glu Arg<br>550 555 560 | 1857 |
| gtt ggg aat acg gtg aat ggt gca gcg agt aga gac aag ttt aag ctg<br>Val Gly Asn Thr Val Asn Gly Ala Ala Ser Arg Asp Lys Phe Lys Leu<br>565 570 575 580 | 1905 |
| ccg tcg tgg gca gag caa atg tat ata gac cat gag cag cag att gtg<br>Pro Ser Trp Ala Glu Gln Met Tyr Ile Asp His Glu Gln Gln Ile Val<br>585 590 595 | 1953 |
| gca taagaagcag aaagaaagat gtgggattta tattgctttt gtcttctggg<br>Ala | 2006 |
| cctctctaca cagaatctaa caaatctggc aataattctt tgatttgtgt ttgacccata | 2066 |
| gtttggttac tagtatatgt ttttttatgt tctttttttc ttagtcattc tcttgtcctt | 2126 |
| cgtgacacta tgtaatgatt aaaagcaaat aattgatgca tgagttcaaa tgttctttga | 2186 |
| aggatccatc ttattagctt tgtaattgtt gtgatatctt aatcttattg gttacgtaaa | 2246 |
| aaaaaaaaaa aaaaaaaaaa aaaaaaa | 2273 |

```
<210> SEQ ID NO 2
<211> LENGTH: 597
<212> TYPE: PRT
<213> ORGANISM: Arabidopsis thaliana
<220> FEATURE:
<221> NAME/KEY: VARIANT
<222> LOCATION: 138
<223> OTHER INFORMATION: Xaa = Any Amino Acid

<400> SEQUENCE: 2

Met Cys Gly Ala Lys Ser Asn Leu Cys Ser Ser Lys Thr Leu Thr Glu
 1               5                  10                  15

Val Glu Phe Met Arg Gln Lys Ser Glu Asp Gly Ala Ser Ala Thr Cys
             20                  25                  30

Leu Leu Glu Phe Ala Ala Cys Asp Asp Leu Ser Ser Phe Lys Arg Glu
         35                  40                  45

Ile Glu Glu Asn Pro Ser Val Glu Ile Asp Glu Ser Gly Phe Trp Tyr
     50                  55                  60

Cys Arg Arg Val Gly Ser Lys Lys Met Gly Phe Glu Glu Arg Thr Pro
 65                  70                  75                  80

Leu Met Val Ala Ala Met Tyr Gly Ser Met Glu Val Leu Asn Tyr Ile
                 85                  90                  95

Ile Ala Thr Gly Arg Ser Asp Val Asn Arg Val Cys Ser Asp Glu Lys
            100                 105                 110

Val Thr Ala Leu His Cys Ala Val Ser Gly Cys Ser Val Ser Ile Val
        115                 120                 125

Glu Ile Ile Lys Ile Leu Leu Asp Ala Xaa Ala Ser Pro Asn Cys Val
    130                 135                 140

Asp Ala Asn Gly Asn Lys Pro Val Asp Leu Leu Ala Lys Asp Ser Arg
145                 150                 155                 160

Phe Val Pro Asn His Ser Ile Lys Ala Val Glu Val Leu Leu Thr Gly
                165                 170                 175

Ile His Gly Ser Val Met Glu Glu Glu Glu Glu Leu Lys Ser Val
                180                 185                 190

Val Thr Lys Tyr Pro Ala Asp Ala Ser Leu Pro Asp Ile Asn Glu Gly
            195                 200                 205

Val Tyr Gly Thr Asp Asp Phe Arg Met Phe Ser Phe Lys Val Lys Pro
    210                 215                 220

Cys Ser Arg Ala Tyr Ser His Asp Trp Thr Glu Cys Pro Phe Val His
225                 230                 235                 240

Pro Gly Glu Asn Ala Arg Arg Arg Asp Pro Arg Lys Tyr Pro Tyr Thr
                245                 250                 255

Cys Val Pro Cys Pro Glu Phe Arg Lys Gly Ser Cys Pro Lys Gly Asp
                260                 265                 270

Ser Cys Glu Tyr Ala His Gly Val Phe Glu Ser Trp Leu His Pro Ala
            275                 280                 285

Gln Tyr Arg Thr Arg Leu Cys Lys Asp Glu Thr Gly Cys Ala Arg Arg
    290                 295                 300

Val Cys Phe Phe Ala His Arg Arg Asp Glu Leu Arg Pro Val Asn Ala
305                 310                 315                 320

Ser Thr Gly Ser Ala Met Val Ser Pro Arg Ser Asn Gln Ser Pro
                325                 330                 335

Glu Met Ser Val Met Ser Pro Leu Thr Leu Gly Ser Ser Pro Met Asn
            340                 345                 350

Ser Pro Met Ala Asn Gly Val Pro Leu Ser Pro Arg Asn Gly Gly Leu
    355                 360                 365
```

-continued

```
Trp Gln Asn Arg Val Asn Ser Leu Thr Pro Pro Leu Gln Leu Asn
    370                 375                 380

Gly Ser Arg Leu Lys Ser Thr Leu Ser Ala Ile Tyr Met Asp Met Glu
385                 390                 395                 400

Met Glu Leu Arg Phe Arg Gly Leu Asp Asn Arg Arg Leu Gly Asp Leu
                405                 410                 415

Lys Pro Ser Asn Leu Glu Glu Thr Phe Gly Ser Tyr Asp Ser Ala Ser
                420                 425                 430

Val Met Gln Leu Gln Ser Pro Ser Arg His Ser Gln Met Asn His Tyr
            435                 440                 445

Pro Ser Ser Pro Val Arg Gln Pro Pro His Gly Phe Glu Ser Ser
        450                 455                 460

Ala Ala Met Ala Ala Ala Val Met Asn Ala Arg Ser Ser Ala Phe Ala
465                 470                 475                 480

Lys Arg Ser Leu Ser Phe Lys Pro Ala Pro Val Ala Ser Asn Val Ser
                485                 490                 495

Asp Trp Gly Ser Pro Asn Gly Lys Leu Glu Trp Gly Met Gln Ile Tyr
                500                 505                 510

Glu Leu Asn Lys Leu Arg Arg Ser Ala Ser Phe Gly Ile His Gly Asn
            515                 520                 525

Asn Asn Asn Ser Val Ser Arg Pro Ala Arg Asp Tyr Ser Asp Glu Pro
        530                 535                 540

Asp Val Ser Trp Val Asn Ser Leu Val Lys Glu Asn Ala Pro Glu Arg
545                 550                 555                 560

Val Asn Glu Arg Val Gly Asn Thr Val Asn Gly Ala Ala Ser Arg Asp
                565                 570                 575

Lys Phe Lys Leu Pro Ser Trp Ala Glu Gln Met Tyr Ile Asp His Glu
                580                 585                 590

Gln Gln Ile Val Ala
        595

<210> SEQ ID NO 3
<211> LENGTH: 13
<212> TYPE: DNA
<213> ORGANISM: Artificial Sequence
<220> FEATURE:
<223> OTHER INFORMATION: 5' primer for construction of substraction
      library of osmotic stress genes

<400> SEQUENCE: 3
aattcggcac gag                                                          13

<210> SEQ ID NO 4
<211> LENGTH: 15
<212> TYPE: DNA
<213> ORGANISM: Artificial Sequence
<220> FEATURE:
<223> OTHER INFORMATION: 3' primer for construction of substraction
      library of osmotic stress genes

<400> SEQUENCE: 4
tttttttttt ttttt                                                        15

<210> SEQ ID NO 5
<211> LENGTH: 17
<212> TYPE: DNA
<213> ORGANISM: Artificial Sequence
<220> FEATURE:
<223> OTHER INFORMATION: 5' primer for PCR of AtSIZ gene
```

```
<400> SEQUENCE: 5
agcaaccttt gctcatc                                                    17

<210> SEQ ID NO 6
<211> LENGTH: 17
<212> TYPE: DNA
<213> ORGANISM: Artificial Sequence
<220> FEATURE:
<223> OTHER INFORMATION: 3' primer of PCR of AtSIZ gene

<400> SEQUENCE: 6
gatggatcct tcaaaga                                                    17

<210> SEQ ID NO 7
<211> LENGTH: 19
<212> TYPE: DNA
<213> ORGANISM: Artificial Sequence
<220> FEATURE:
<223> OTHER INFORMATION: right border primer for PCR of T-DNA

<400> SEQUENCE: 7
tcgggcctaa cttttggtg                                                  19

<210> SEQ ID NO 8
<211> LENGTH: 19
<212> TYPE: DNA
<213> ORGANISM: Artificial Sequence
<220> FEATURE:
<223> OTHER INFORMATION: left border primer for PCR of T-DNA

<400> SEQUENCE: 8
gaacatcggt ctcaatgca                                                  19
```

TRANSCRIPTIONAL FACTOR ENHANCING THE RESISTANCE OF PLANTS TO OSMOTIC STRESS

TECHNICAL FIELD

The present invention relates to a transcription factor of a plant, AtSIZ, induced by osmotic stress; a gene encoding the transcription factor; and a method for enhancing stress resistance in plants by using the gene.

BACKGROUND ART

Environmental stresses such as high concentration of salt, drought and cold inhibit plant growth to limit harvest yields in many important agricultural fields. In terms of these stresses, osmotic stress caused by diverse external conditions, for example, high salt, dehydration and cold, is a crucial problem for farmers.

Therefore, with even a slight increase of tolerance to such osmotic stress, it is expected that there would be a considerable improvement in agricultural productivity and yield of crops. For this reason, much research into regulatory mechanisms of plants, with respect to osmotic stress, and regulatory factors involved in the mechanism, have been ongoing. Recent studies have revealed that plants employ elaborate mechanism to partially adapt to osmotic stress, and one of important requirements for such stress-adaptation is the transcriptional activation of a gene encoding a protein necessary to such adaptation (Jang et al., *Plant Mol. Biol.,* 37: 839–847, 1998; Liu et al., *Science,* 280: 1943–1945, 1998; Pardo et al., *Proc. Natl. Acad. Sci.* USA, 95: 9681–9686, 1998; Lie et al., *Proc. Natl. Acad. Sci.* USA, 97: 3730–3734, 2000).

Many genes induced by certain stresses were isolated, and their characteristics have been widely studied, being helpful to understand mechanisms involved in adaptation to osmotic stress. From these studies, it has become clear that there are multiple signaling pathways that lead to induction of osmotic stress responsive genes (Jonak et al., *Proc. Natl. Acad. Sci.* USA, 93: 11274–11279, 1996; Ishitani et al., *Plant Cell* 9: 1935–1949, 1997), and these pathways include ABA (abscisic acid)-dependent or ABA-independent pathway (La Rosa et al., *Plant Physiol.,* 85: 174–181, 1987; Savoure et al., *Mol. Gen. Genet.,* 254: 104–109, 1997). In addition, it was discovered that some signaling pathways are common to all osmotic stress conditions, such as high salt, dehydration and cold (Jang et al., *Plant Mol. Biol.,* 37: 839–847, 1998; Liu et al., *Science,* 280: 1943–1945, 1998; Pardo et al., *Proc. Natl. Acad. Sci.* USA, 95: 9681–9686, 1998; Lie et al., *Proc. Natl. Acad. Sci.* USA, 97: 3730–3734, 2000).

As described above, transcriptional control plays a pivotal role in the adaptation responses and is likely to be regulated by specific transcription factors, and several stress-inducible genes encoding such transcription factors or their homolgues have been isolated and characterized (Tague et al., *Plant Mol. Biol.* 28: 267–279, 1995; Bastola et al., *Plant Mol. Biol.,* 24: 701–713, 1998; Kasuga et al., *Nat. Biotechnol.,* 17: 287–291, 1999; van Der Krol et al., *Plant Physiol.,* 121: 1153–1162, 1999; Nakashima et al., *Plant Mol. Biol.,* 42: 657–665, 2000). Further research provided information that transcription factors encoded by several genes of the discovered genes have a zinc finger motif. Examples of such transcription factors include Atmyb2, ATHB-7, mlip15 (Kusano et al., *Mol. Gen. Genet.,* 248: 507–517, 1995; Soderman et al., *Plant J.* 10: 375–381,1996), Alfin1 (Bastola et al., *Plant Mol. Biol.,* 24: 701–713, 1998) and AZF1, AZF2 and AZF3 (Sakamoto et al., *Gene,* 248: 23–32,2000).

Specifically, Atmyb2 in the *Arabidopsis* plant is induced by dehydration stress, and then bound to a conserved MYB recognition sequence, and induction of an *Arabidopsis* homeobox gene ATHB-2 is caused by dehydration or abscisic acid treatment. Mlip15 in corn is a transcription factor isolog having a bZIP motif, and is induced at low temperature. Alfin1, a zinc finger protein, is induced by salt stress and has an MsPRP2 promoter-binding site. The Alfin1 protein plays an important role in regulating MsPRP2 expression in the root of alfalfa and consequently contributes to the salt-tolerance in this plant. There is a recent report in which a gene family coding a DRE/CRT binding protein was isolated and characterized (Liu et al., *Plant Cell,* 10: 1391–1406, 1998). According to the report, such a gene family includes DREB1 (dehydration-inducible element binding protein) and DREB2, which binds to 9 consensus sequences found in promoter regions of a variety of dehydration- or low temperature-inducible genes such as RD29A, Cor6.6 and RD17. However, the transcription factors described above are just a part of the factors constituting a large group of transcription factors involved in a response to osmotic stress.

Since, with respect to such stress-inducible genes, transcription factors can regulate their transcriptions, they may be useful to construct a plant resistant to stress by causing the transcription factors to be overexpressed or inhibited in the plant.

SUMMARY OF THE INVENTION

Accordingly, the present inventors have conducted studies to find a novel gene involved in resistance of plants to environmental stress, particularly, osmotic stress. As a result, they found that a novel protein, AtSIZ, which is isolated from *Arabidopsis thaliana* and has zinc finger motifs, exhibits a regulatory activity on transcription of stress-inducible genes, and is further capable of enhancing resistance of the plant to osmotic stress upon overexpression of a gene coding AtSIZ.

Thus, it is an object of the invention to provide a novel plant transcription factor induced by osmotic stress, which induces expressions of diverse stress-inducible genes.

It is another object of the invention to provide a gene encoding the transcription factor and an eukaryotic expression vector comprising the gene.

It is yet another object of the invention to provide a method for enhancing resistance of a plant to osmotic stress by transformation of the plant with the gene.

In accordance with one aspect of the present invention, the above and other objects can be accomplished by the provision of a plant transcription factor, AtSIZ comprising the amino acid sequence of SEQ ID NO: 2 having 597 amino acid residues.

The transcription factor, AtSIZ is isolated from *Arabidopsis thaliana*, and has three $C_3H$-type zinc finger motifs at amino acid residues 211 through 325. It has a transcription activation domain at the C-terminal region. Further. AtSIZ activates transcriptions of a variety of genes induced by osmotic stress, for example, COR15a (cold-regulated protein) which confers resistance to cold, and RD29 which confers resistance to dehydration, cold and high concentrations of salt.

AtSIZ shows the same ability to promote transcription of stress-induced genes when approximately 207 amino acid residues are deleted from its C-terminal region. With an additional deletion of 45 amino acid residues, however, its transcription-promoting activity is significantly reduced. For this reason, it is expected that the region containing amino acid residues 345 through 390 plays a critical role in AtSIZ transcription regulatory activity. Moreover, a part of the AtSIZ protein consisting of amino acid residues 1 through 390 with a deletion of amino acid residues 391 through 597 at its C-terminus can be used in constructing a plant resistant to osmotic stress. In accordance with the invention, there is thus provided a part of AtSIZ protein consisting of amino acid residues 1 through 390 of the amino acid sequence of SEQ ID NO: 2.

In accordance with another aspect of the present invention, there is provided an AtSIZ gene encoding the transcription factor, AtSIZ. The gene has a nucleotide sequence represented by SEQ ID NO: 1 and is induced by osmotic stress, especially, a high concentration of NaCl.

When a mutation occurs in the AtSIZ gene, a plant becomes sensitive to osmotic stress. As a result, the mutant plant accumulates anthocyanin in its leaves and has broken leaf edges, and small and etiolated leaves are seen. On the other hand, plants which overexpress AtSIZ show a high survival rate even under conditions where a wild type plant cannot survive, due to osmotic stress upon being treated with a high concentration of NaCl.

Finally, in accordance with yet another aspect of the present invention, there is provided a method for enhancing resistance of a plant to osmotic stress by introducing an AtSIZ gene to the plant, constructing a transformed plant which overexpresses the gene. Using the method, productivity of the plant can be considerably increased. For transformation, the AtSIZ gene may be a full-length cDNA of AtSIZ or a partial gene encoding a part (amino acid residues 1 through 390) of the AtSIZ protein comprising only a region exhibiting transcription-promoting ability of stress-inducible genes.

The term "osmotic stress-inducible gene" or "osmotic stress-responsive gene" as used herein refers to a gene encoding a protein induced by osmotic stress caused by exposure of the plant to a high concentration of salt, low temperature, dehydration, or exogenous ABA treatment; or a gene involved in exhibiting tolerance or resistance to osmotic stress. The term "AtSIZ-complement" refers to a recombinant vector comprising an active AtSIZ gene, which can express the transcription factor AtSIZ in an AtSIZ-inactivated mutant. The term "AtSIZ-complemented mutant" refers to a mutant plant transformed with the AtSIZ-complement.

Additionally, a description herein referring to a gene encoding AtSIZ, the transcription factor, is in italic, that is, "AtSIZ gene" or "AtSIZ", while the protein encoded by the gene is represented as "AtSIZ protein" or "AtSIZ".

The above and other objects, features and other advantages of the present invention will be more clearly understood from the following detailed description taken in conjunction with the accompanying drawings.

BRIEF DESCRIPTION OF THE DRAWINGS

FIG. 1 shows a comparison of amino acid sequences of other zinc finger containing proteins, with respect to an amino acid sequence of AtSIZ deduced from a nucleotide sequence of an AtSIZ gene (SEQ ID NOS: 2 and 9–11).

FIG. 9b shows results of β-galactosidase activity assays in yeast transformed with the respective diverse lengths of AtSIZ, as represented in FIG. 9a.

DETAILED DESCRIPTION OF THE INVENTION

Figure 2:
FIG. 2 shows Northern blot analysis of an expression pattern of an AtSIZ gene in diverse plant tissues such as flower (F), leaf (L), root (R) and silique (S).
Figure 2:
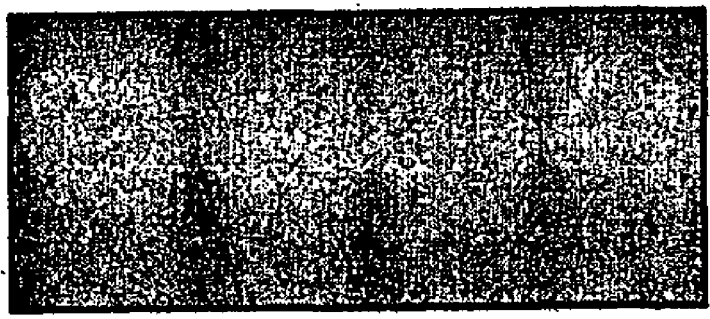

The inventors intended to isolate a novel gene induced by osmotic stress. Control cDNAs derived from a plant not exposed to stress were subjected to hybridization with individual single cDNAs from a cDNA library of a plant exposed to high salt stress. Thus, constitutively expressed cDNAs in the plant were subtracted, constructing a subtraction library.

More specifically, the control cDNAs were labeled with biotin. Then, they were subjected to hybridization with individual single cDNAs obtained from the cDNA library which comprises cDNAs induced by salt stress. Based on a binding property of biotin to streptavidin, the hybridized cDNAs were removed by applying a membrane coated with streptavidin. Through the course of removal, the residual single cDNAs are genes specifically induced by stress from a high concentration of salt, and were subsequently subjected to sequencing analysis. As a result, 15 clones of genes expressed by osmotic stress were found. Among the clones found, a novel clone whose nucleotide sequence was not known, OS183, was employed as a probe for finding a full-length cDNA. The full-length cDNA was isolated. The cDNA has a size of 2267 bp with a putative molecular weight of approximately 66 kDa and an open reading frame encoding 597 amino acids, which was designated as AtSIZ (*Arabidopsis thaliana* Stress-Induced Zinc finger).

Figure 1:
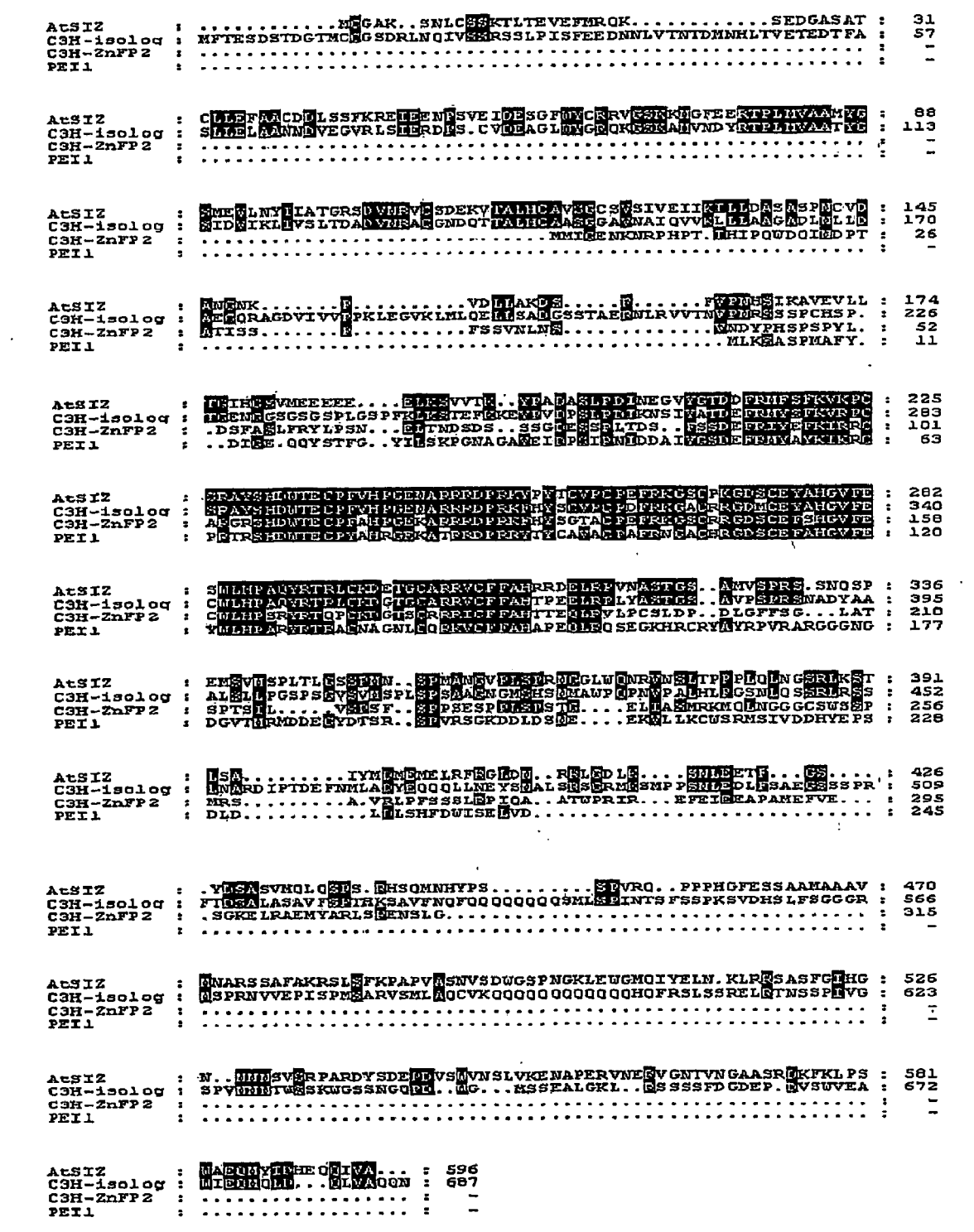

A nucleotide sequence of the AtSIZ gene is represented by SEQ ID NO: 1, and an amino acid sequence of an AtSIZ protein deduced therefrom is represented by SEQ ID NO: 2. The AtSIZ protein encoded by the gene shares high homology with other proteins having zinc finger motifs (see FIG. 1). It has $C_3H$ type zinc finger motifs comprising a consensus sequence of $CX_7CX_5CX_3H$ (C is Cysteine, H is Histidine and X is any amino acid) in the middle of the amino acid sequence. In addition, AtSIZ has an acidic region with 6 consecutive glutamate residues located upstream of the zinc finger region.

In an embodiment of the invention, with the aim of examining expression patterns of the AtSIZ, total RNAs were isolated from tissues of flowers, leaves, roots of *Arabidopsis thaliana* and siliques, respectively, and subjected to Northern blot analysis. It was seen that AtSIZ is expressed at different levels according to the tissues, and the root tissues show the highest level of expression, followed by the flower and leaf tissues in order, but there is little expression in silique tissues (see FIG. 2). Meanwhile, since AtSIZ was first isolated where the *Arabidopsis* plant was treated with a relatively high concentration of NaCl, it might be necessary to also examine its expression patterns according to intensity and variety of osmotic stress. Seedlings of *Arabidopsis* were exposed to a higher concentration of NaCl, dehydration, cold and exogenous abscisic acid (ABA), respectively, and subjected to Northern blot analysis. The results showed that though there were differences in AtSIZ expression levels, its expression was commonly induced by all the above treatments, demonstrating that AtSIZ is involved in a response to general osmotic stress. Further, considering that their expression patterns varied according to the stress conditions, it was found that the expression of AtSIZ is regulated according to certain stress conditions (see FIG. 3).

In another embodiment of the invention, it was found that when a mutation occurs in the AtSIZ gene, the mutant plant is sensitive to NaCl stress, while when the AtSIZ is overexpressed, the plant shows an increased resistance to NaCl stress.

Figure 4:
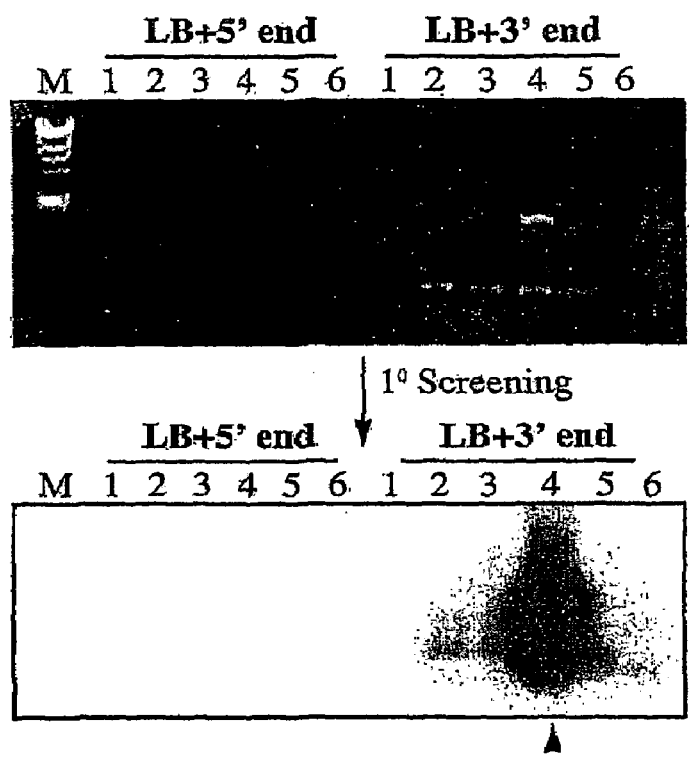
FIG. 4 shows results of PCR screening and Southern blot analysis for selecting and confirming a mutant harboring a T-DNA insert within an AtSIZ gene and a location of the T-DNA insert in AtSIZ, based on the result of nucleotide sequencing: A) is a agarose gel of primary PCR products, wherein LB represents a primer specific for the left border of T-DNA; B) is a agarose gel of tertiary PCR products; and C) shows a location of T-DNA within AtSIZ in a selected mutant harboring T-DNA.
Figure 4:
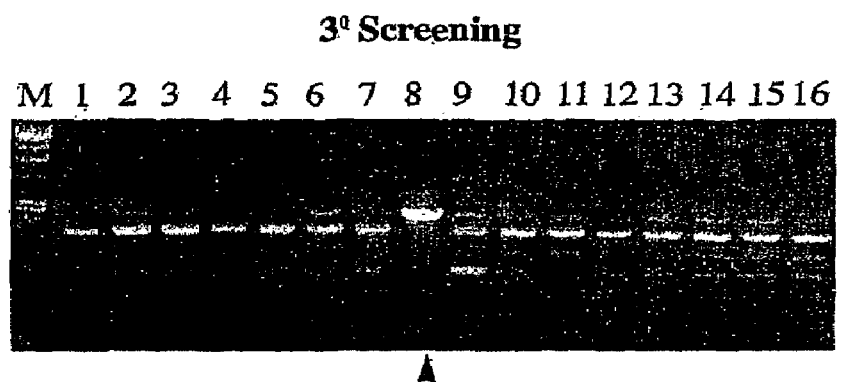
Figure 4:
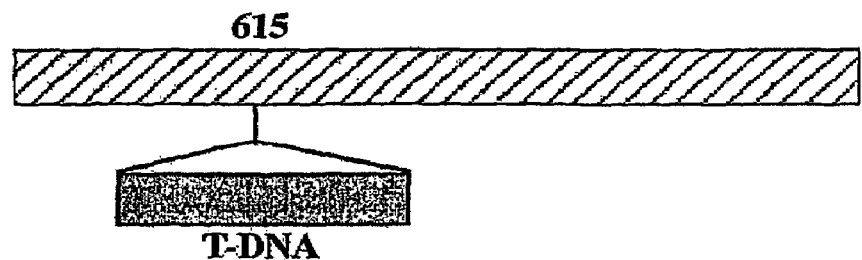

Specifically, a mutant plant which harbors a T-DNA within AtSIZ was selected from transformed plants (ABRC, USA) harboring a T-DNA insert. With respect to individual genomic DNAs obtained from the group of the transformed plants, PCR was performed using a combination of a primer specific for the 3'-end or 5'-end of the AtSIZ gene and a primer specific for the T-DNA right border (RB) or T-DNA left border (LB). Then, a Southern blot was prepared using a labeled AtSIZ cDNA as a probe for hybridization with the PCR products. As shown in FIG. 4, where a combination of primers specific for LB of the T-DNA and 3'-end of AtSIZ were used, an amplified PCR product was hybridized with an AtSIZ cDNA, indicating that a T-DNA was inserted within AtSIZ. With sequencing, the identity of the PCR product thus obtained was confirmed and the location of the inserted T-DNA was determined. It was found that T-DNA was inserted at nucleotide 615 of the AtSIZ gene.

Using the selected mutant plant whose AtSIZ was mutated via T-DNA insertion, physiological roles of the AtSIZ gene were examined. Such mutant plants were exposed to a variety of stress conditions, and their phenotypes were examined. The mutant plants accumulated anthocyanin in their leaves. While wild type plants showed no response to the concentration of 25 mM NaCl, the mutant plants had broken leaves at their edges. In addition, with a higher concentration of NaCl, the leaves of the mutants were smaller than those of wild type plants and had the yellow phenotype. These results demonstrate that the mutant plants, which had a mutation in AtSIZ, are much more sensitive to NaCl stress than the wide-type plants. Accordingly, this indicates that AtSIZ is involved in resistance to NaCl stress.

In another embodiment of the invention, a complementation test was carried to clearly confirm the physiological activities of AtSIZ. That is, complementation ability of the mutants was tested to prove that such phenotype changes of the mutant plants were attributed to a T-DNA insertion in the AtSIZ gene.

An AtSIZ cDNA was inserted in pBIB-HYG, a binary vector carrying a hygromycin resistance marker so as to construct an AtSIZ complement. The complement was introduced to the mutant plant which has a mutation in AtSIZ caused by a T-DNA insertion, using an *Agrobacterium*-mediated vacuum infiltration method. Northern blot was performed to confirm the AtSIZ complementation. It was seen that AtSIZ of the AtSIZ-complemented mutant plant was expressed at a high level. With respect to a wild type plant, the sensitivities of AtSIZ-inactivated mutant and AtSIZ-complemented mutant plants, to NaCl stress were compared. The AtSIZ-complemented mutant plant exhibited NaCl resistance at a level similar to the wild type plant (see FIG. 6). These results demonstrate that the NaCl sensitivity phenotype of the AtSIZ-inactivated mutant is due to a T-DNA insertion in the AtSIZ gene.

In another embodiment of the invention, it was examined whether AtSIZ, a transcription factor, is involved in regulating transcription of other genes induced by NaCl stress. As stress-inducible genes, there are COR15a and RD29A, whose expression can be induced by exogenous ABA treatment or a variety of osmotic stresses.

COR15a is one of COR genes (cold-regulated) found in plants which undergo cold adaptation, and it is possible that their gene products may be involved in freezing resistance (Artus et al., *Proc. Natl. Acad. Sci.* USA, 93(23): 13404–13409, 1996). According to a recent report, constitutive expression of COR15a raises a survival rate of *Arabidopsis* under cold conditions. A low temperature induces disruption of both the physical continuity and permeability of the plasma membrane, which is responsible for osmotic control. Such damage allows substances in the cytoplasm and organelles to leak, and causes fusion of the cell membrane with an endomembranes, for example, outermembrane of chloroplasts, thereby lowering freezing resistance. COR15a is a stress-inducible gene raising a survival rate of plants by attenuating responses of the cell membrane and chloroplast to freezing.

RD29 is a gene of the *Arabidopsis* plant whose expression is induced by dehydration, cold, or a high concentration of salt. There are two kinds of RD29A and RD29B. A promoter of RD29A exists in most organelles and tissues of plants growing where moisture is deficient, such that the plants have increased resistance to dehydration stress (Yamaguchi et al., *Mol. Gen. Genet.*, 236: 331–340, 1993).

Expression levels of COR15a and RD29A in wild type, AtSIZ-inactivated mutant and AtSIZ-complemented mutant plants, in response to a high concentration of NaCl and cold stress, were examined. A mutation of AtSIZ specifically inhibited induction of COR15a expression in response to NaCl stress, while failing to inhibit its expression in response to cold stress (see FIG. 7). On the other hand, RD29A expression was highly induced in the AtSIZ-inactivated mutant in response to NaCl or cold stress, indicating that a mutation in AtSIZ does not affect RD29A expression induction by NaCl or cold stress. These results strongly imply that AtSIZ is involved in induction of expression of stress-inducible genes, specifically in response to NaCl stress.

Involvement of AtSIZ in the response to NaCl stress is further supported by an experiment using a plant overexpressing AtSIZ. A transformed plant which expresses AtSIZ at a level of 10 to 20 times higher than a wild type plant showed increased resistance to stress from a high concentration of NaCl (see FIG. 8).

Figure 9A:
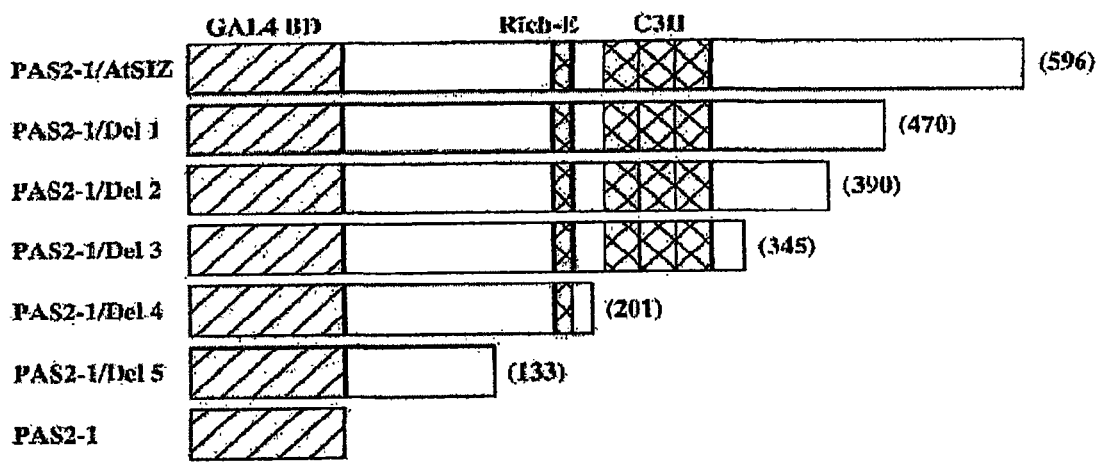
FIG. 9a is a schematic diagram showing GAL4-AtSIZ fused constructs having deletions at their C-terminal regions, which have diverse lengths of AtSIZ fragments linked to a gene encoding a GAL4 DNA-binding domain (GAL4 BD), wherein Rich-E represents a region rich in glutamate residues.

In yet another embodiment of the invention, the activity of the AtSIZ protein as a transcription factor and its active site were determined. Using a yeast 1-hybrid technique, it was proved that AtSIZ has transcription promoting activity. The hybrid technique is based on the fact that, if AtSIZ has transcription activating ability, when AtSIZ is expressed so as to bind to a GAL4 DNA-binding protein, a reporter gene, gal1-LacZ transcription would be activated. In yeast, AtSIZ activated transcription of gal1-LacZ, demonstrating that AtSIZ has transcription promoting activity. The deletion test showed that where 207 amino acid residues are deleted from the C-terminal of the AtSIZ amino acid sequence of SEQ ID NO: 2, the transcription-promoting activity of AtSIZ is not changed. An additional deletion of 45 amino acid residues, however, significantly reduced its transcription-promoting activity. For this reason, it is expected that the region containing amino acid residues 345 through 390 plays a critical role in the transcription activation activity of AtSIZ (see FIG. 9a and FIG. 9b). Thus, a part of the AtSIZ protein consisting of amino acid residues 1 through 390 can be used for increasing resistance to osmotic stress in plants.

Hereinafter, the present invention will be described in detail, in conjunction with various examples. These examples are provided only for illustrative purposes, and the present invention is not to be construed as being limited to those examples.

EXAMPLE 1

Cultivation of *Arabidopsis thaliana*

All *Arabidopsis* plants used in experiments of the invention were cultivated in a culture room at 22° C. or a green house controlled to maintain a cycle of 16 hrs light/8 hrs darkness and 70% relative humidity. The seedlings were cultured on Murashige-Skoog (MS) agar plates, or for a chemical treatment, in 250 ml culture flasks containing MS liquid media while stirring at 100 rpm. The plant tissues of choice were collected and immediately frozen under liquid nitrogen.

EXAMPLE 2

Isolation of Osmotic Stress-inducible Genes

To isolate genes whose expressions are induced by osmotic stress, especially, salt stress, a subtraction library was constructed, and then cDNAs were randomly selected from the library and screened by sequencing them. For the subtraction library, cDNAs derived from plants exposed to salt stress were subjected to hybridization with cDNAs derived from the control plant which was not exposed to salt stress, thereby subtracting the constitutively expressed cDNAs.

2-1: Culture of the *Arabidopsis* Plant

The *Arabidopsis* plants were cultured under the same conditions as in Example 1. After 1 week, with the purpose of obtaining stress-induced cDNAs, the seedlings were exposed to salt stress by changing the media with MS media containing 0.15 M NaCl. The seedlings were cultured for an additional 1 to 6 hrs while stirring. All seedlings were immediately frozen and stored at −80° C.

2-2: Extraction of RNA and Construction of cDNA Library

To prepare an osmotic stress-derived cDNA library, total RNA was first extracted from the frozen seedling which was treated with 0.15 M NaCl for 6 hrs, using a lithium chloride/phenol extraction method. The total RNA was treated according to the protocol of an mRNA isolation kit (Pharmacia, USA) to isolate poly(A)$^+$ RNA. As a control, salt-untreated seedlings were subjected to the above procedure to isolate poly(A)$^+$ RNA. Then, with respect to osmotic stress-derived cDNA, the cDNA library was constructed using a cDNA synthesis kit (Stratagene, USA). The individual cDNAs were ligated to λ ZAP II (Stratagene, USA), finally constructing a λ ZAP II cDNA library.

2-3: Construction of Subtraction Library

With regard to the λ ZAP II cDNA library, a quantity of filamentous phages were obtained, and individual single stranded DNAs were purified therefrom. To remove clones bearing constitutively expressed cDNAs from the λ ZAP II cDNA library derived from the stress-applied plant, subtraction was performed by hybridization with the control cDNA.

To label the control cDNA with biotin, an excess amount of double stranded cDNA prepared above was subjected to PCR incorporating biotinylated dUTP.

In detail, 100 ng of the control double cDNA was employed as a template. As for primers, oligonucleotides having the nucleotide sequences of SEQ ID NO: 3 and SEQ ID NO: 4, respectively, were synthesized and 50 ng each was employed. 50 µM of biotin-16-dUTP was supplied in a PCR reaction mixture, thereby producing biotin-labeled cDNA. The PCR condition was 30 sec at 94° C., 30 sec at 38° C., 30 sec at 72° C., and 50 cycles thereof.

To subtract constitutively expressed cDNAs, hybridization was carried out. 0.1 µg of the single stranded cDNA from the λ ZAP II cDNA library and 1 µg of the biotinylated control cDNA probe were added to a hybridization cocktail (containing 50 mM Tris-HCl, pH 7.5, 0.25 M NaCl and 1.0 mM EDTA) at 65° C. overnight. The hybridization solution was incubated with membranes coated with streptavidin on ice for 2 hrs with occasional stirring, followed by removing the membranes. Since streptavidin has a high affinity for biotin, cDNA samples hybridized with the biotinylated control cDNA can be removed by eliminating the membranes coated with streptavidin. That is, after hybridization, only cDNAs which are specifically expressed by salt stress remained in the hybridization solution. These cDNAs were extracted by employing phenol/chloroform and chloroform. Then, the cDNAs were added with 2 μg carrier tRNA and cold ethanol at −20° C., thereby being precipitated. The cDNAs thus obtained were transfected to an *E. coli* host cell by electroporation method. In this way, the subtraction library was prepared. In such a library, clones were randomly selected, and their DNA sequences were analyzed using an automatic sequencer.

From the sequencing analysis, 15 osmotic stress-inducible ESTs (Expressed Sequence Tags) were found. Among these, 4 cDNAs were found to be novel genes. Specifically, the clone carrying a 0.8 kb DNA was employed in experiments thereafter.

EXAMPLE 3

Isolation of AtSIZ cDNA

An amino acid sequence deduced from the nucleotide sequence of said clone was subjected to homology search using NCBI's Blast program. The amino acid sequence showed a high degree of homology to other proteins having zinc finger motifs. Database search revealed that the sequence shares 55.7% homology with $C_3H$-isolog, 23.7% with $C_3H$-Znfp2, and 19.1% with PEI1, as represented in FIG. 1. Therefore, the inventors designated the protein expressed by the gene isolated above as AtSIZ (*Arabidopsis thaliana* Stress-Induced Zinc Finger).

Since the cDNA clone has a part of the gene AtSIZ, it is required to find a clone carrying full-length AtSIZ. To obtain the full-length gene, an AtSIZ insert was employed as a probe to screen the .lambda. ZAP II cDNA library constructed in Example 2. One clone carrying the full-length cDNA was isolated. The cDNA has a size of 2267 bp (SEQ ID NO: 1) with a putative molecular weight of approximately 66 kDa and an open reading frame encoding 597 amino acids. The full-length cDNA was subcloned to pBluescript, constructing a recombinant plasmid. The recombinant plasmid was transformed to *E. coli*, and the transformed cell was deposited in the Korean Collection for Type Cultures (KCTC) affiliated to Korea Research Institute of Bioscience and Biotechnology (KRIBB), #52, Oun-dong, Yusong-ku, Taejon, 305–333, Republic of Korea, under deposit No. KCTC 0886BP on Nov. 3, 2000.

An amino acid sequence of AtSIZ protein which is deduced from the full-length cDNA, was subjected to homology comparison using a BlastX program of NCBI. The comparison was performed between amino acid sequences of $C_3H$-isolog (protein accession No. g1871192), $C_3H$-Znfp2 (g3643609), and PEI1 (g2961542). It was seen that homology with respect to the above proteins having zinc finger motifs is highest in the middle region of the amino acid sequence involving zinc finger motifs (see FIG. 1). Referring to FIG. 1, the amino acids identical to amino acids for AtSIZ were marked with black color. Based on the analysis result, the zinc finger region of the deduced protein AtSIZ has a consensus sequence of $CX_7CX_5CX_3H$, demonstrating $C_3H$-type zinc finger. In addition, AtSIZ has an acidic region with 6 consecutive glutamate residues upstream of the zinc finger region.

EXAMPLE 4

Induction of AtSIZ Expression by Diverse Osmotic Stresses

To determine functions of AtSIZ, expression patterns of AtSIZ by diverse osmotic stresses in diverse tissues were examined.

4-1: Expression Patterns According to Diverse Tissues

Total RNAs were isolated from tissues of flowers, leaves, roots and siliques, respectively, using a LiCl/phenol method. Northern blot was prepared to assess the transcription levels in these tissues, employing AtSIZ cDNA as a probe. 15 μg total RNA from each tissue was heat-treated at 65° C. for 15 min to loosen its secondary structure, mixed with formaldehyde gel loading buffer (50% glycerol, 1 mM EDTA, pH 8.0, 0.25% bromophenol blue, 0.25% xylene cyanol FF in distilled water). Each sample was loaded on 1% agarose gel containing 2.2 M formaldehyde, followed by slow electrophoresis at a voltage of 4 V/cm. The gel with developed RNAs was immersed in $DEPC-H_2O$ to remove formaldehyde. Then, the gel was transferred to a nylon membrane by capillary transfer for about 16 hrs, followed by heat treatment at 80° C. for 1 hr, thereby immobilizing RNAs. As a probe for hybridization, AtSIZ cDNA was labeled with [$\alpha$-$^{32}$P] dCTP with the aid of a random primer labeling kit (Boeringer Mannheim, Germany). That the same amount of respective total RNAs was loaded into each well in the gel was confirmed by staining with ethidium bromide. Finally, for the detection of hybridization, the membrane was exposed to X-ray film at −70° C. The results are shown in FIG. 2. It was seen that AtSIZ is expressed at different levels according to the tissues. The root tissues show the highest level of expression, followed by the flower and leaf tissues in order, but there is little expression in silique tissues.

4-2: Expression Patterns According to Osmotic Stress Variety

Figure 3:
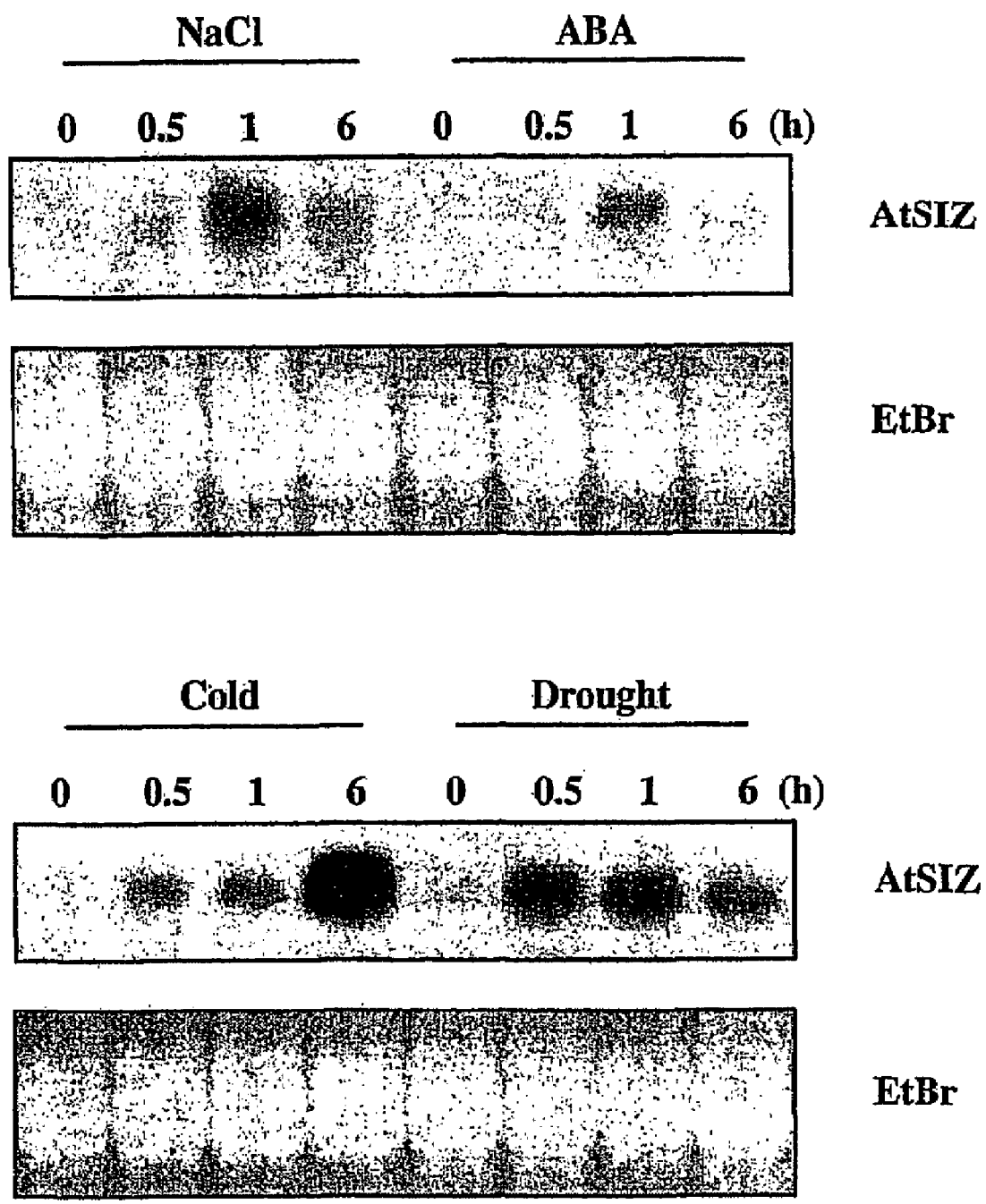
FIG. 3 shows Northern blot analysis of an expression pattern of an AtSIZ gene induced by diverse osmotic stresses (the numerals represent treatment time of osmotic stress).

In addition to the effect of 0.15 M NaCl on the expression of AtSIZ in *Arabidopsis* plant, the expression patterns were further examined according to osmotic stress intensity and variety. The seedlings of *Arabidopsis* were exposed to a high salt concentration of 150 mM NaCl, dehydration, a low temperature of 4° C. and exogenous abscisic acid (ABA), respectively. Total RNAs were isolated and subjected to Northern blot analysis using an analogous method as in Example 4-1. The results are shown in FIG. 3. The expression of AtSIZ was induced by all the above treatments, indicating that AtSIZ is involved in responses to general osmotic stress. Despite such a common expression of AtSIZ, its expression pattern was different according to the stress conditions. As for the exogenous ABA and 150 mM NaCl treatment, the expression showed a peak 1 hr after each treatment, followed by a decrease thereafter. As for the low temperature treatment, the expression was induced at a low level at first, followed by a large increase 6 hours after treatment, implying that there are at least two mechanisms for the expression induction of AtSIZ by a low temperature stress. On the other hand, as for the dehydration treatment, the expression showed a peak within 30 min after treatment and such an expression level was maintained for more than 6 hrs after treatment. Therefore, these results demonstrate that the expression of AtSIZ is regulated at a variable level according to stress conditions.

EXAMPLE 5

Isolation of an *Arabidopsis* Mutant Plant with T-DNA Inserted in AtSIZ Gene It is necessary to compare a wild type plant with an AtSIZ gene-inactivated plant to understand physiological roles of AtSIZ.

To select a mutant having T-DNA inserted within an AtSIZ gene, a PCR screening method (McKinney et al., *Plant J.*, 4: 613–622, 1995) was used to probe genomic DNAs (ABRC, USA) of a group of transformed plants harboring a T-DNA tag. The three round PCR screening was performed using a combination of primers specific for the 3'-end and 5'-end (SEQ ID NO: 5 and SEQ ID NO: 6, respectively) of the AtSIZ gene of SEQ ID NO: 1 and primers specific for the T-DNA right border (RB) and T-DNA left border (LB)(SEQ ID NO: 7 and SEQ ID NO: 8, respectively). As for respective templates, individual genomic DNAs (ABRC, USA) obtained from a group of transformed plants harboring T-DNA inserts were employed.

The PCR product thus obtained was subjected to Southern blot analysis employing a $^{32}$P labeled AtSIZ cDNA as a probe for detecting hybridization. The result is shown in FIG. 4; A. Using a combination of primers specific for LB of T-DNA and 3'-end of AtSIZ, an amplified PCR product was found, indicating that the PCR product has a T-DNA insert within an AtSIZ gene. In this way, the transformed plant having a T-DNA inserted within an AtSIZ gene was selected.

Confirmation of disruption of the AtSIZ gene in such a transformed plant was carried out by Southern blot analysis of genomic DNA obtained therefrom (Data not shown). Moreover, a transformation marker gene, npt II, was employed as a probe in performing a Southern blot to confirm that there is only one copy of T-DNA in the genome of the plant (Data not shown). Meanwhile, an inactivated homozygous mutant plant was selected relying on kanamycin resistance, and its DNA was extracted, followed by PCR amplification to confirm a T-DNA insertion.

To prove that said PCR product is identical to the AtSIZ gene, and a location of the T-DNA insertion, the PCR product was subcloned to a pBluescript vector, followed by sequencing. It was found that T-DNA was inserted at nucleotide 615 of the AtSIZ cDNA sequence (See FIG. 4; C).

EXAMPLE 6

Determination of Phenotype of T-DNA Insertion Mutant

Phenotype of mutant plants was examined for determining physiological role of AtSIZ.

First, total RNA was extracted from the homozygous mutant and wild type plants subjected to Northern blot analysis to confirm no expression of AtSIZ in mutant plants.

Figure 5:
FIG. 5 is a result of examining phenotype of T-DNA insertion mutant: A) shows Northern blot analysis of expression patterns of AtSIZ in a T-DNA insertion mutant (mt) and a wild type (WT), and B) shows comparisons of phenotypes in leaves of plants cultivated after treatment with varying concentrations of NaCl (b, c and d represent 25, 50 and 100 mM, respectively), with respect to the plant cultivated under general growth condition (a), wherein the numerals 2, 4, 6 and 8 represent a $2^{nd}$, $4^{th}$, $6^{th}$, and $8^{th}$ leaf from the base of the plants, respectively.
Figure 5:
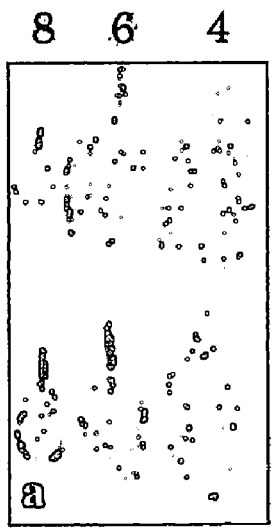
Figure 5:
Figure 5:
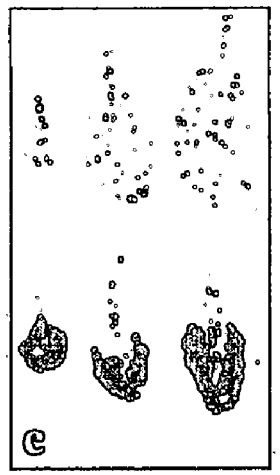
Figure 5:

Wild type (WT) and mutant (mt) plants were cultivated in soil for 3 weeks, and thereafter, the plants were cultured in liquid media with a treatment of variable concentrations of NaCl for 10 days. As for the mutants, although no expression of AtSIZ was found by Northern blot (FIG. 5; A), little difference of phenotype could be seen as compared to wild type (WT) plants, when grown in soil under a general growth conditions. However, the mutants were highly sensitive to NaCl stress. The mutant plants accumulated anthocyanin in their leaves. Where the plants were treated with 25 mM NaCl, WT plants did not show any response, while levels of mutant plants develpoed broken edges (FIG. 5; B, lower part of panel b). Also, where the plants were treated with 50 mM NaCl, WT plants did not show any response to the stress (FIG. 5; B, upper part of panel c), while mutant plants had smaller leaves than those of WT, and the leaves were yellow (FIG. 5; B, lower part of panel c). Further, where the plants were treated with 100 mM NaCl, mutant plants had smaller leaves with strong etiolation, while the leaves of WT plants were a little etiolated in their edges. These results demonstrate that the mutant plants are much more sensitive to NaCl stress than the wild type plants.

EXAMPLE 7

Complementation Test

The mutant plants were isolated from transgenic lines inserted with T-DNA. Therefore, complementation ability of the mutants was tested to prove that such osmotic stress-sensitive phenotypes of the mutant plants were attributable to a T-DNA insertion in the AtSIZ gene.

7-1: Construction of an AtSIZ Complement and Production of an AtSIZ-complemented Mutant using the Complement An AtSIZ cDNA was inserted in pBIB-HYG, a binary vector carrying a hygromycin resistance marker gene (Becker D., Institut für Genetic der Universitat zu Koln, FRG, *Nucleic Acid Res.*, 180(1): 203, 1990) so as to construct an AtSIZ complement.

First, the AtSIZ subcloned in pBluescript was digested with Xho I, and the 5-overhang of the Xho I site was filled in with a mixture of Klenow and dNTPs to make a blunt ended DNA. Then, the DNA was restricted with Xba I to yield an AtSIZ insert. The insert was ligated into an Xba I/Ecl 136 II site of pBIB-HYG vector, ensuring that the insert is located between the CaMV 35S promoter and the Nos terminator, thereby constructing a recombinant vector capable of expressing a transcription factor encoded by AtSIZ.

Figure 6:
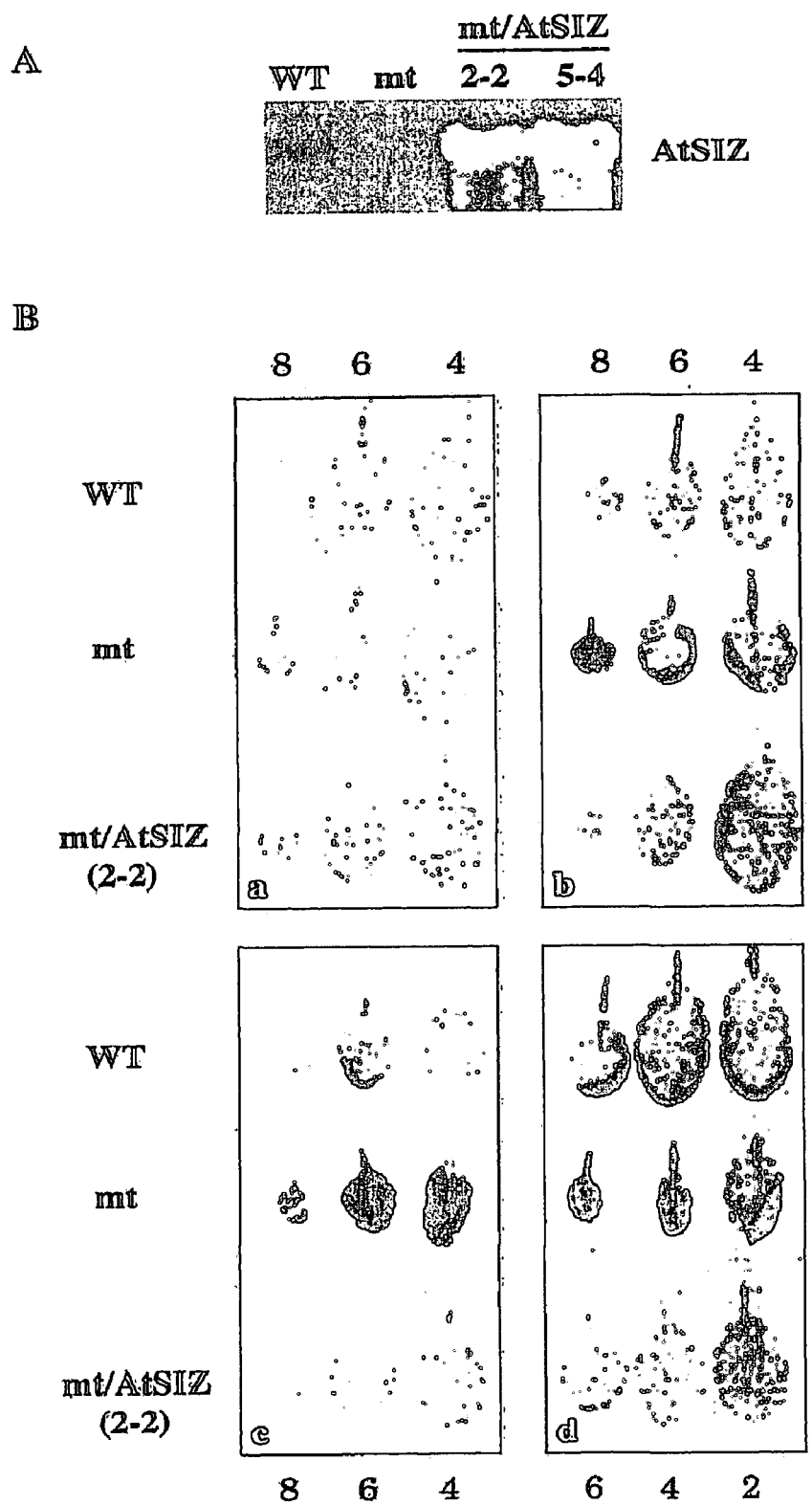
FIG. 6 is a result of examining the sensitivity to NaCl stress by complementing AtSIZ cDNA into T-DNA insertion mutant: A) shows Northern blot analysis of AtSIZ expressed in a T-DNA-complemented mutant plant (mt/AtSIZ), a T-DNA insertion mutant (mt) and a wild type (WT) and B) shows comparisons of phenotypes in leaves of the plants cultivated after treatment with varying concentrations of NaCl (a, b, c and d represent 0, 25, 50 and 100 mM, respectively), wherein the numerals 2, 4, 6 and 8 represent a $2^{nd}$, $4^{th}$, $6^{th}$, and $8^{th}$ leaf from the base of the plants, respectively.

The recombinant vector thus constructed was used to transform a mutant plant harboring an inactivated AtSIZ gene. Using an Agrobacterium-mediated vacuum infiltration method (Clough et al., *Plant J.*, 16: 735–743, 1998), the mutant plant was transformed, whereby the transcription factor AtSIZ can be complemented. The transformed plants were selected on a MS plate containing 50 μg/ml hygromycin. Such selected plants were transferred to soil, and their seeds were obtained. These seeds were again selected on a hygromycin containing MS plate. In this way, homozygous T2 lines of AtSIZ-complemented mutants were obtained. Total RNA was extracted from wild type, mutant and the AtSIZ-complemented homozygous T2 mutant plants, followed by Northern blot analysis employing $^{32}$P-labeled AtSIZ cDNA as a probe. FIG. 6; A shows that AtSIZ-complemented homozygous T2 mutant lines 2-2 and 5-4 contain large amounts of transcripts of the AtSIZ gene, while the AtSIZ-inactivated mutant contains few of the transcripts.

7-2: NaCl Stress Sensitivity Test of AtSIZ-complemented Mutant Plants

Ability of the AtSIZ-complemented homozygous mutant plants to resist NaCl stress was examined by measuring the sensitivity to NaCl stress at various NaCl concentrations. Wild type, mutant and AtSIZ-complemented homozygous T2 mutant (line 2-2) plants were cultivated in soil for 3 weeks. Then, the plants were immersed in 0, 25, 50 and 100 mM NaCl solutions, respectively, every 3 days, followed by drying and culturing them. These steps were repeated through 10 days.

As shown in FIG. 6; B, the AtSIZ-complemented homozygous mutant plants exhibited NaCl tolerance at a level similar to the wild type plants. This demonstrates that phenotype of AtSIZ-inactivated mutants against NaCl stress can be changed by an AtSIZ complement. That is, it was proved that NaCl sensitivity of the AtSIZ-inactivated mutants is due to T-DNA insertion in AtSIZ.

EXAMPLE 8

Effect of AtSIZ on Activation of Transcription of Stress Inducible-genes

On the basis of the experimental results showing that sensitivity to NaCl stress increases in AtSIZ-inactivated mutants, it was examined whether AtSIZ is involved in regulating transcription of other genes whose expressions are induced by NaCl stress. Total RNAs were extracted from wild type, mutant and AtSIZ-complemented mutant plants, respectively, followed by Northern blot analysis.

Each of the plants above was cultured in a liquid MS medium for 1 week, and exposed to 150 mM NaCl and a low temperature of 4° C. for 6 hrs. As stress-inducible genes, COR15a and RD29A (Urao et al., Plant Cell, 5: 1529–1539, 1993; Baker et al., Plant Mol. Biol., 24: 701–713, 1994), served as reporter genes. Their expressions can be induced by exogenous ABA treatment or a variety of osmotic stresses. Northern blot analysis was performed employing $^{32}$P-labeled cDNAs of AtSIZ, COR15a (Thomashow M. F., GenBank accession No. U01377), and RD29A (Yamaguchi-Shinozaki, GenBank accession No. D13044) as probes.

Figure 7:
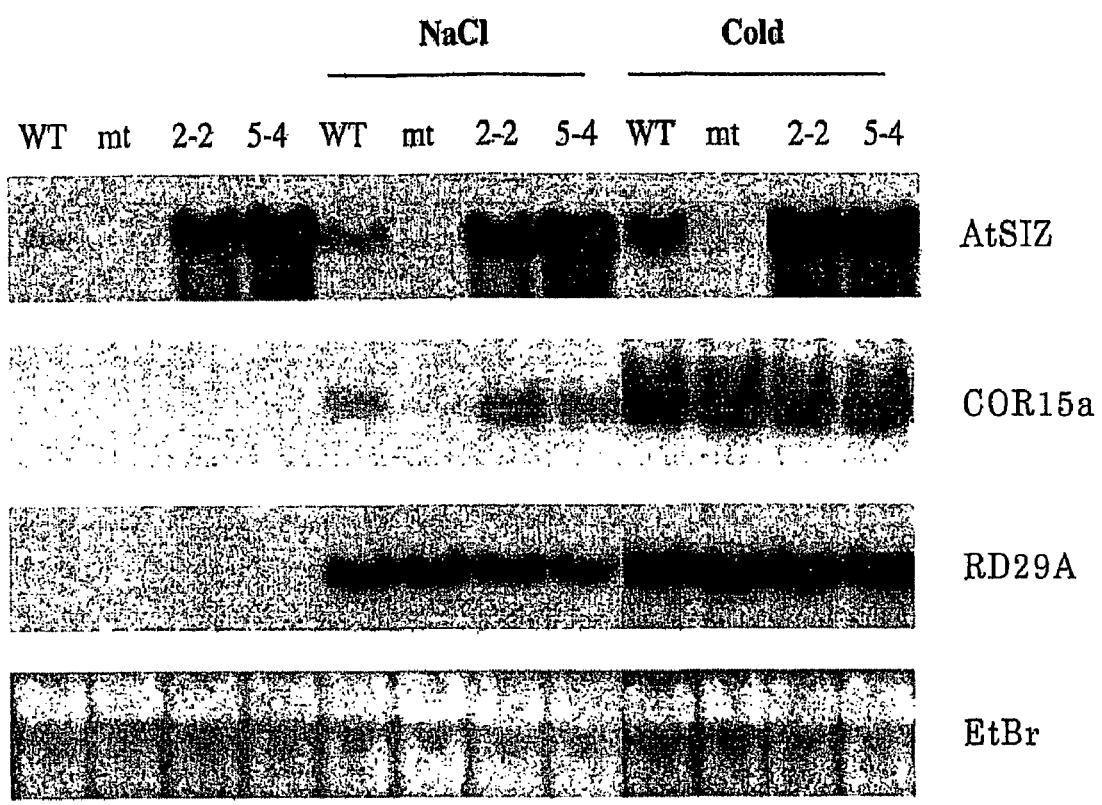
FIG. 7 shows Northern blot analysis of expression patterns of AtSIZ, COR5a and RD29A in a wild type (WT), a T-DNA insertion mutant (mt) and T-DNA-complemented mutant plants (2-2 and 5-4 represent independent mutant lines thereof), wherein NaCl refers to 6 hrs treatment with 150 mM NaCl, and cold refers to 6 hrs treatment of a low temperature of 4° C.

Expression patterns of COR15a and RD29A in AtSIZ-inactivated mutant and AtSIZ-complemented mutant plants, in response to NaCl and cold stress, were examined. The results are shown in FIG. 7. As for COR15a, a strong expression induction was seen in AtSIZ-complemented mutants, while AtSIZ-inactivated mutants failed to induce the expression in response to NaCl stress. On the other hand, in response to cold stress, COR15a expression was strongly induced in the AtSIZ-inactivated mutants as well as AtSIZ-complemented mutants, showing that a mutation in AtSIZ does not affect COR15a expression induction by cold stress. As for RD29A, the expression was highly induced in the AtSIZ-inactivated mutants as well as AtSIZ-complemented mutants in response to NaCl or cold stress, indicating that a mutation in AtSIZ does not affect RD29A expression induction by NaCl or cold stress.

Consequently, it is demonstrated that AtSIZ has an effect of transcription activation of certain osmotic stress-inducible genes, specifically in response to NaCl stress.

EXAMPLE 9

Increase of Stress Resistance of a Plant Due to AtSIZ Overexpression

It was confirmed that the AtSIZ gene is involved in response to NaCl stress by the results mentioned above. Therefore, a transformed plant which overexpresses AtSIZ was constructed, and its resistance to NaCl stress was examined.

First, to construct a recombinant vector carrying an AtSIZ gene, AtSIZ cDNA was inserted in a pBI121 binary vector (Dr. Goodman, Harvard Medical School, Genetics Department) having a CaMV (Cauliflower mosaic virus) 35S promoter, replacing a GUS (β-glucuronidase) coding region. Vacuum infiltration was performed to transfer the recombinant vector to a wild type Arabidopsis plant. A detailed protocol is described as follows. The AtSIZ subcloned in pBluescript was digested with SpeI, and the 5-overhang was filled in with a mix of Klenow and dNTPs to make a blunt ended DNA. Then, SmaI was used to restrict the DNA to yield an AtSIZ insert. The insert was ligated into pBI121 which was restricted with SmaI and Ecl 136 II, ensuring that the insert is located between the CaMV 35S promoter and the Nos transcription terminator, thereby constructing a recombinant binary plasmid, pBI121-AtSIZ capable of over-expressing AtSIZ.

Figure 8:
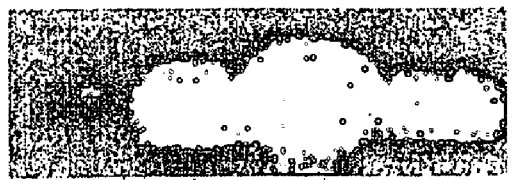
FIG. 8 shows Northern blot analysis of expression patterns of AtSIZ in a wild type (WT) and T-DNA-complemented mutant plants (1-6, 2-4 and 19-4 represent independent mutant lines thereof) (A); and a photograph showing plants exhibiting different sensitivities to NaCl (B).
Figure 8:
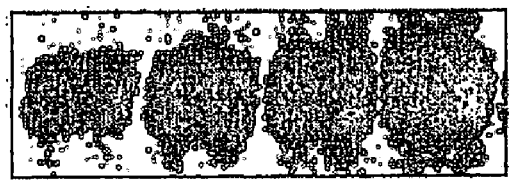
Figure 8:
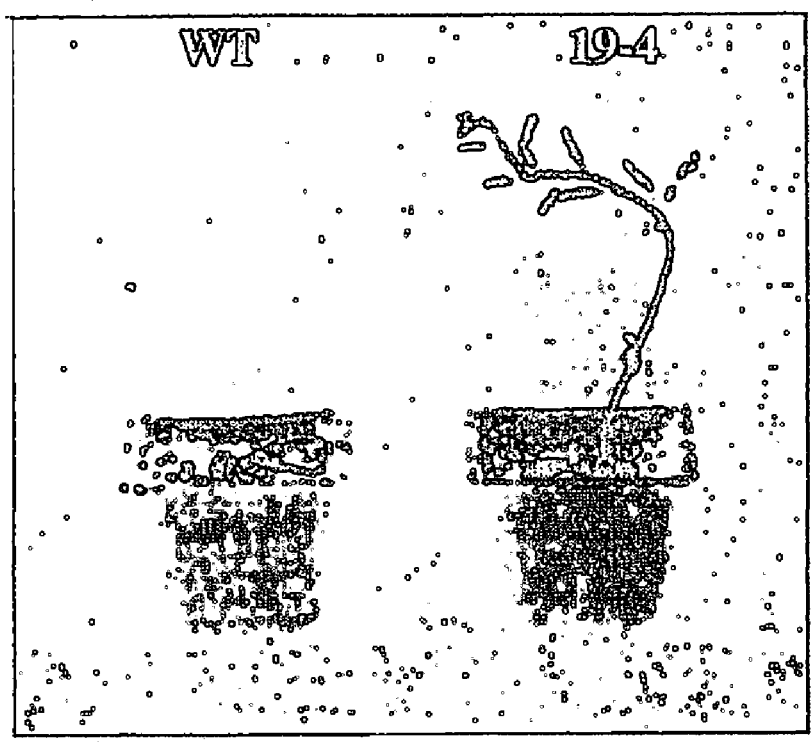

The recombinant plasmid thus constructed was used to transform Arabidopsis plants via vacuum infiltration. For transformation, the wild type plants were grown in pots for 4 weeks at 22° C. First bolts were clipped off. Infiltration was performed when secondary bolts had a length of 2 to 10 cm. Meanwhile, 3 days after clipping the first bolts, a colony of Agrobacterium transformed with the pBI121-AtSIZ was precultured overnight in a 5 ml LB broth, followed by culturing in a 500 ml LB medium until its turbidity reached to 2.0 at $OD_{600}$. The cells were harvested by centrifugation at 5,500×g and resuspended to 0.8 at $OD_{600}$ in a 5% sucrose solution. The suspension was added with a surfactant, Silwet L-77 to a final concentration of 0.05%, and the solution was transferred to a beaker. The pots were inverted so only the above-ground parts of the plants were immersed in the Agrobacterium solution for 30 seconds. The pots were removed, laid on their side and let stand in the dark for 24 hrs. The next day, the pots were placed upright and cultivated in a green house at 22° C. until seeds were mature. Dry seeds were harvested. The transformed plants were selected on a MS plate containing 50 mg/L kanamycin. In this way, homozygous T2 lines of AtSIZ-overexpressing mutants were obtained. Total RNA was extracted from the plants, followed by Northern blot analysis employing $^{32}$P-labeled AtSIZ cDNA as a probe. FIG. 8; A shows that the transgenic lines 1-6, 2-4 and 19-4 exhibit strong AtSIZ expression, indicating that the AtSIZ insert was highly expressed.

Responding to a high concentration of NaCl stress, such AtSIZ-overexpressing mutant plants were examined for their phenotypes. The plants were cultivated for 2 weeks and treated with 200 mM NaCl every 3 days. Phenotypes were observed 10 days after treatment. FIG. 8; B shows appearances of a wild type (WT) and a transgenic line 19-4 plants. For reference, other transgenic lines had the same appearance as the lineage 19-4, so they are not presented in FIG. 8. With respect to the plants, NaCl resistance was quantified. Their seeds were treated with 300 mM NaCl for 10 days and then sown. 20 plants each of wild type and AtSIZ-overexpressing mutant were tested in three independent experiments. The respective mean data are represented in FIG. 8; B. The AtSIZ-overexpressing plants showed resistance to the high concentration of NaCl, and specifically, 3 week-cultivated plants survived at a rate of about 70% (resistance 70±5), while wild type plants failed to survive. These results demonstrate that AtSIZ is involved in the plant's adaptability to intense NaCl stress.

EXAMPLE 10

Analysis of Functional Domains of the Transcription Factor, AtSIZ

Sequencing of AtSIZ gave information that AtSIZ encodes C₃H-type zinc finger polypeptides. Here, it was determined whether an AtSIZ protein acts as a transcription factor, like other zinc finger-containing proteins, and identified which regions activate transcription. A deletion analysis of the AtSIZ gene was carried out. Sequential deletions from the C-terminal of the AtSIZ protein were made, individually inserted in a vector, pAS2-1 downstream of a region encoding a GAL4 DNA binding domain and then, effect of such deletions was assessed using Yeast 1-hybrid system (Clonetech, USA). In detail, each of the full-length sequence (amino acid residues 1–597) and diverse lengths of C-terminal-deleted sequences (amino acid residues 1–470, 1–390, 1–345, 1–201 and 1–133) was inserted into the BamHI site of pAS2-1 (Clonetech, USA), ensuring that it could be expressed as a fusion protein linked to a 3'-end of the GAL4 binding domain. The recombinant vectors thus constructed and a control pAS2-1 were respectively introduced to a yeast strain, Y190 (Clontech, USA), and then tryptophan positive clones were selected as transformants. Using a color development assay method (Li et al., *Science*, 262: 1870–1874, 1993), the transcription activation of the gene coding β-galactosidase was examined. The selected yeast cells were placed on Whatman 3 MM filter paper and soaked with X-gal solution, then let stand at room temperature for 3 hrs, thereby color being developed.

Figure 9B:
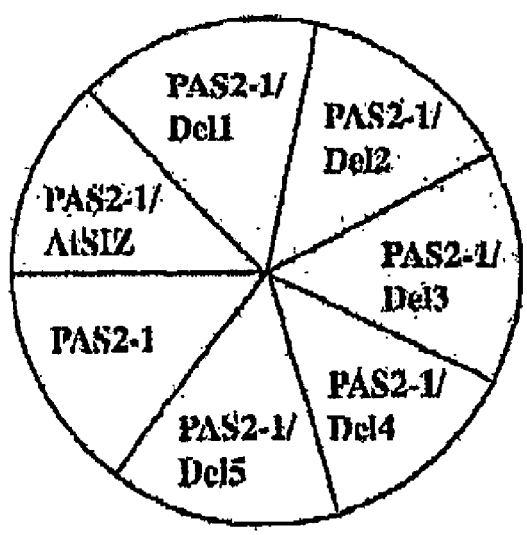
Figure 9B:
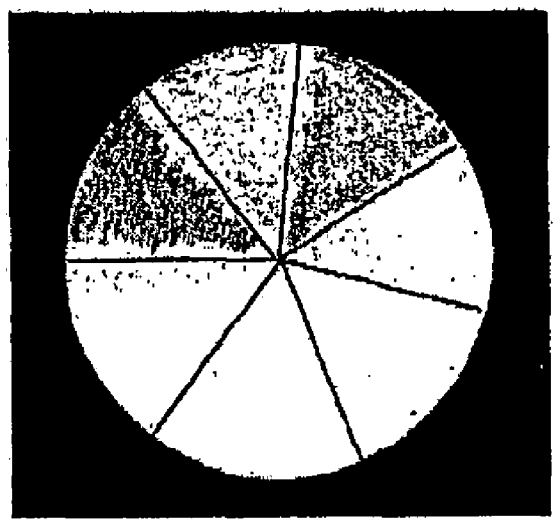

As shown in FIG. 9b, it can be seen that the full-length AtSIZ protein was fused with the GAL4 DNA-binding domain so it strongly induced expression of β-galactosidase. This result demonstrates that AtSIZ is a strong transcription factor. Where 207 amino acids were deleted from the C-terminus (that is, Del 1 and Del 2), no changes in transcription-activation activity were seen. On the other hand, where an additional deletion of 45 amino acid residues was made (that is, Del 3; corresponding to amino acid residues 1–345 of a sequence of SEQ ID NO: 2), such a deletion construct showed a very low induction level of β-galactosidase. Moreover, where the zinc finger region was deleted (that is, Del 4; amino acid residues 1–201), no β-galactosidase activity was exhibited. Therefore, these results demonstrate that AtSIZ plays a role as a transcription factor in plant cells. Further, it is clear that 207 amino acids from the C-terminus of the AtSIZ amino acid sequence of SEQ ID NO: 2 are not necessary for the transcription regulating activity.

INDUSTRIAL APPLICABILITY

As apparent from the above description, the present invention provides a novel transcription factor induced by osmotic stress, which is a protein designated as AtSIZ and having zinc finger motifs, its gene being AtSIZ. Inactivation of AtSIZ makes a plant sensitive to osmotic stress, while overexpression thereof confers the plant with resistance to osmotic stress. Further, AtSIZ exhibits activity as a transcription factor with respect to certain osmotic stress-inducible genes, its active site being revealed herein. Accordingly, it is possible to transform a plant with an expression vector carrying the AtSIZ, making the plant overexpress AtSIZ, thus constructing a plant resistant to osmotic stress. Consequently, it is possible to accomplish a considerable increase in plant productivity.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

---

What is claimed is:

1. An isolated nucleic acid encoding a polypeptide comprising amino acid residues 1–390 of the amino acid sequence of SEQ ID NO: 2, wherein said polypeptide retains the activity of SEQ ID NO: 2 of conferring enhanced resistance to osmotic stress when expressed in a transgenic plant.

2. The isolated nucleic acid according to claim 1, wherein the isolated nucleic acid comprises the nucleotide sequence of SEQ ID NO: 1.

3. An eukaryotic expression vector comprising the isolated nucleic acid according to claim 1.

4. The eukaryotic expression vector according to claim 3, wherein the vector comprises an isolated nucleic having the nucleotide sequence of SEQ ID NO: 1, wherein said vector has been deposited with KCTC under the accession number: KCTC 086BP.

5. A method for enhancing resistance to osmotic stress in a plant, comprising transforming the plant with the expression vector according to claim 3 so as to overexpress said transcription factor in said plant, wherein said overexpression results in enhanced resistance to osmotic stress in said plant.

6. The method according to claim 5, wherein the osmotic stress includes stress induced by salt, temperature, dehydration or abscisic acid treatment.

7. A transformed plant whose resistance to osmotic stress is enhanced by the method according to claim 5.

8. An isolated nucleic acid encoding a polypeptide having the amino acid sequence of SEQ ID NO: 2.

9. An eukaryotic expression vector comprising the nucleic acid according to claim 8.

10. A method for enhancing resistance to osmotic stress in a plant, comprising transforming the plant with the expression vector according to claim 9, so as to overexpress said polypeptide in said plant, wherein said overexpression results in enhanced resistance to osmotic stress in said plant.

11. The method according to claim 10, wherein the osmotic stress includes stress induced by salt, temperature, dehydration or abscisic acid treatment.

12. A transformed plant having the expression vector according to claim 9 introduced therein, wherein said transcription factor is overexpressed in said plant and said overexpression results in enhanced resistance to osmotic stress in said plant.

* * * * *